(12) United States Patent
Nabeshima et al.

(10) Patent No.: US 6,210,690 B1
(45) Date of Patent: Apr. 3, 2001

(54) EMULSION COMPOSITION

(75) Inventors: Hisaya Nabeshima; Yasunari Nakama; Takayuki Omura, all of Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/147,171

(22) PCT Filed: Mar. 3, 1998

(86) PCT No.: PCT/JP98/00864

§ 371 Date: Oct. 23, 1998

§ 102(e) Date: Oct. 23, 1998

(87) PCT Pub. No.: WO98/38970

PCT Pub. Date: Sep. 11, 1998

(30) Foreign Application Priority Data

Mar. 4, 1997 (JP) .................................... 9-065310

(51) Int. Cl.$^7$ ................ A61K 7/00; A61K 7/06; A61K 31/695

(52) U.S. Cl. ............ 424/401; 424/70.1; 516/53; 516/55; 514/63

(58) Field of Search .................. 424/401, 70.1; 516/53, 55; 514/63

(56) References Cited

U.S. PATENT DOCUMENTS

| 5,429,820 | * | 7/1995 | Kamitani et al. | 424/401 |
|---|---|---|---|---|
| 5,472,686 | * | 12/1995 | Tsubaki et al. | 424/59 |
| 5,578,311 | * | 11/1996 | Nagatani et al. | 424/401 |

* cited by examiner

*Primary Examiner*—Thurman K. Page
*Assistant Examiner*—Amy E Pulliam
(74) *Attorney, Agent, or Firm*—Townsend & Banta

(57) ABSTRACT

A water-in-oil type emulsified composition containing one or more types chosen from among a group consisting of one or more types of a specific polyether modified silicone, oil, water or water and ethyl alcohol as well as a water soluble polymer with a molecular weight of 2,000–300,000 whose content is 0.1–20 wt % of the total emulsified composition, an inorganic salt or amino acid salt whose content is 0.1–08 wt % of the total emulsified composition. It is possible to provide an emulsified composition which gives gloss to the hair or skin, is moist but not sticky and exhibits excellent stability by using, as the emulsifier, polyether modified silicone rather than a surfactant or an organic modified clay mineral.

10 Claims, No Drawings

EMULSION COMPOSITION

FIELD OF THE INVENTION

This invention relates in general to an emulsified composition, and more particularly to an water-in-oil type emulsified composition which gives gloss to hair or skin, is moist but not sticky and exhibits excellent stability.

BACKGROUND OF THE INVENTION

Silicone polymers are known to have superior water repellency, heat resistance and acid resistance and are frequently used in various industrial materials. In particular, they give gloss and have a refreshing texture without stickiness when used for cosmetic materials or quasi-drug materials and therefore they are used in various applications including skin care cosmetics, makeup cosmetics and hair cosmetics.

However, in order to obtain a stable emulsion, a surfactant or an organic modified clay mineral has to be blended in, and this deteriorates the non-sticking and refreshing feeling during use which is characteristic of silicone polymers, resulting in stickiness.

That is, it is difficult in terms of the emulsion stability to obtain a water-in-oil type emulsion by using only a silicone polymer for an emulsifier without additionally using a surfactant or an organic modified clay mineral. A solution for this problem is desired.

In order to solve this shortcoming, attempts have been made by, for example, using a polyether modified silicone for the emulsifier (Japanese examined patent publication Tokko Hei 5-32363) or by blending in various additives. However, this problem has not been solved up to this point.

The inventors conducted earnest investigation in view of the aforementioned problems and discovered that an emulsified composition which gives gloss to hair or skin, is moist but not sticky and exhibits excellent stability could be provided by using a water-in-oil type emulsion which contains high molecular weight polyether modified silicone with a specific polyoxyalkylene group content as a silicone polymer emulsifier and water soluble polymer, inorganic salt or amino acid salt for its stabilizer, thus completing the present invention.

The object of the present invention is to provide an emulsified composition which is moist but not sticky and exhibits excellent stability by using, for the emulsifier, polyether modified silicone rather than a surfactant or an organic modified clay mineral.

DISCLOSURE OF THE INVENTION

That is, the present invention provides an water-in-oil type emulsified composition containing one or more types chosen from among a group consisting of (I) one or more types of polyether modified silicone represented by the following general formula [Chemical formula 1], (II) oil, (III) water or water and ethyl alcohol and (IV) a water soluble polymer with a molecular weight of 2,000–300,000 whose content is 0.1–20 wt % of the total emulsified composition, 0.1–8 wt % inorganic salt or amino acid salt.

[Chemical formula 1]

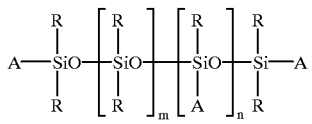

(In this formula, A denotes a group chosen from among a group consisting of a methyl group, phenyl group and a polyoxyalkylene group represented by the general formula —$C_3H_6O(C_2H_4O)_a(C_3H_6O)_bR'$ (where R' denotes a group chosen from among a group consisting of a hydrogen atom, acyl group and alkyl group with a carbon number of 1–4, a denotes an integer 5–50 and b denotes an integer 5–50) and at least one of the three A's is an polyoxyalkylene. R denotes a methyl group or phenyl group, m denotes an integer 50–1,000 and n denotes an integer 1–40. The polyether modified silicone molecule contains 40 wt % or more of polyoxyalkylene groups and the molecular weight of the polyether modified silicone is 30,000 or more.)

The present invention also provides said waterin-oil type emulsified composition wherein said water soluble polymer is polyethylene glycol, said amino acid salt is sodium glutamate and said inorganic salt is sodium chloride, potassium chloride, magnesium chloride, calcium chloride, aluminum chloride, sodium sulfate, potassium sulfate, magnesium sulfate or aluminum sulfate.

The present invention also provides said waterin-oil type emulsified composition which contains hydrophobic powder.

The present invention also provides said waterin-oil type emulsified composition wherein said emulsified composition is a skin cosmetic.

The present invention also provides said waterin-oil type emulsified composition wherein said emulsified composition is a hair cosmetic.

BEST EMBODIMENTS OF THE INVENTION

The configuration of the present invention is described in detail below.

The polyether modified silicone used for the emulsifier in the present invention is organop olysiloxane containing polyoxyalkylene groups represented by the aforementioned [Chemical formula 1]. In the present invention, a commercial product (TS Polymer 50-IP from Toray Dow-Corning Silicone Co., Ltd.) can be used.

At least one of the three A's in the aforementioned [Chemical formula 1] of the polyether modified silicone has to be a polyoxyalkylene group represented by the general formula —$C_3H_6O(C_2H_4O)_a(C_3H_6O)_bR'$ and 40 wt % or more of polyoxyalkylene groups have to be contained in the polyether modified silicone molecules. Specific examples of the acyl group for R' in the polyoxyalkylene group include a formyl group, acetyl group, propionyl group, butyroyl group, acryloyl group, benzoyl group and toluoyl group, and specific examples of the alkyl group with a carbon number of 1–4 include a methyl group, ethyl group, i-propyl group, n-propyl group, t-butyl group and n-butyl group. In the polyoxyalkylene group, if a or b is less than 5, then the polyether modified silicone will not exhibit a sufficient emulsifying effect. If a or b is more than 50, then the obtained emulsified composition will be sticky. The polyoxyalkylene group content is 40 wt % or more, and preferably in the range of 40–70 wt %. This is because the capability to emulsify nonpolar oil other than silicone oil decreases when the polyoxyalkylene group content is less than 40 wt %, and the obtained emulsified composition becomes sticky when it is more than 70 wt %. m is an integer 50–1,000 and n is an integer 1–40. This is because the emulsifying effect is not sufficient if m is less than 50 and n is less than 1, and the obtained emulsified composition becomes sticky if m is more than 1,000 and n is more than 40.

The molecular weight of the polyether modified silicone used in the present invention is 30,000 or more, and preferably 50,000 or more. This is because the capability to emulsify nonpolar oil other than silicone oil decreases when the molecular weight of the polyether modified silicone is less than 30,000.

The blend ratio of the polyether modified silicone used in the present invention is not limited in particular, but a preferable range is 0.1–30 wt %, and a more preferable range is 1–15 wt %. If the content of the polyether modified silicone is less than 0.1 wt % then stable emulsification becomes difficult and if it is more than 30 wt % then the emulsified composition may become sticky.

The oil ingredient used in the present invention is not limited in particular, and any oil which is used in emulsified compositions can be used. Examples of the silicone oil include diorgano polysiloxanes with low to high viscosity such as dimethyl polysiloxane, methylphenyl polysiloxane, methylhydrogen polysiloxane and dimethyl siloxane/methylphenyl polysiloxane copolymer, cyclic siloxanes such as octamethylcyclotetrasiloxane, decamethylcyclopentasiloxane and tetramethyltetraphenyltetracyclosiloxane, cyclic siloxane solutions such as high polymer gum-like dimethyl polysiloxane, gum-like dimethylsiloxane/methylphenylsiloxane copolymer and gum-like dimethyl polysiloxane, diorgano polysiloxane containing alkyl groups with a carbon number of 6–50 such as trimethylsiloxy silicic acid and cyclic siloxane solutions of trimethylsiloxy silicic acid, and modified silicone oils such as amino modified silicone, alkyl modified silicone and perfluoroalkyl modified silicone. Examples of the non polar oil include hydrocarbon type oils such as squalane, liquid paraffin, light liquid paraffin, liquid isoparaffin, light isoparaffin, light liquid paraffin and heavy liquid isoparaffin.

The blend ratio of the oil ingredient in the emulsified composition of the present invention is not limited in particular, but should preferably be 80 wt % or less of the total emulsified composition. Typically 3–80 wt % is used.

The blend ratio of water or water and ethyl alcohol used in the present invention is preferably 1–90 wt % and more preferably 3–80 wt %. The blend ratio is less than 1% then the product becomes a transparent gel and an emulsified composition cannot be obtained. If the content is more than 90 wt % then water separates from the emulsion and a stable emulsion cannot be obtained. In this invention, the water-in-oil type emulsified composition refers to those whose non-continuous phase is a water phase or water-ethanol mixed solution phase.

Examples of the water soluble polymer used for the stabilizer in the present invention include synthetic polymers such as polyethylene glycol, polyvinyl alcohol, polyacrylic acid, carboxymethyl cellulose, polyvinyl pyrolidone, hydroxymethyl cellulose and methyl cellulose and natural water soluble polymers including dextrin, pectin, arginic acid and chondroitin sulfuric acid. Their molecular weight is 2,000–300,000, preferably 3,000–100,000. Those with a molecular weight of less than 2,000 do not contribute to stabilization of the emulsion. If the molecular weight is more than 300,000 then the contribution to stabilization is less and there arises a shortcoming in that the emulsified composition feels sticky during use.

The blend ratio of the water soluble polymer is 0.1–20 wt %, preferably 0.5–10 wt %, of the total emulsified composition. If it is less than 0.1 wt % then the emulsion cannot be stabilized. It is not preferable if it is more than 20 wt % because then the emulsified composition feels sticky during use.

Particularly preferable among the water soluble polymers is polyethylene glycol. Polyethylene glycol has advantages in that it is more effective at stabilizing the emulsified composition than the others and that its feeling during use as an emulsified composition is favored. A particularly preferable molecular weight range of polyethylene glycol is 3,000–20,000. A particularly preferable range of the blend ratio is 1–10 wt % of the total emulsified composition.

The amino acid salt used for the stabilizer in the present invention is an amino acid with its carboxyl group or amino group forming a salt. Examples include sodium aspartate, potassium aspartate, magnesium aspartate, calcium aspartate, sodium glutamate, potassium glutamate, magnesium glutamate, calcium glutamate, glutamic acid hydrochloride, cysteine hydrochloride, hystidine hydrochloride, lysine hydrochloride, ornithine hydrochloride, ornithine acetic acid salt, tryptophane hydrochloride, arginine-glutamic acid salt, ornithine-glutamic acid salt, lysine-glutamic acid salt, lysine-aspartic acid salt and ornithine-aspartic acid salt. Among them, sodium glutamate is preferable. The blend ratio of the amino acid salt in the present invention is 0.1–8 wt %, preferably 0.5–5 wt %, of the total emulsified composition. The blend ratio ranges less than 0.1 wt % and more than 8 wt % are not preferable because then the emulsion cannot be stabilized.

Examples of the inorganic salt used as the stabilizer in the present invention include alkali metal salts, alkali earth metal salts, aluminum salts, zinc salts and ammonium salts of hydrochloric acid, sulfuric acid, nitric acid, carbonic acid, phosphoric acid, etc. Examples of the preferable inorganic salts include chlorides such as sodium chloride, potassium chloride, magnesium chloride, calcium chloride, aluminum chloride, zinc chloride and ammonium chloride, sulfates such as sodium sulfate, potassium sulfate, magnesium sulfate, aluminum sulfate, zinc sulfate and ammonium sulfate, nitrates such as sodium nitrate, potassium nitrate, magnesium nitrate, aluminum nitrate, zinc nitrate and ammonium nitrate, carbonates such as sodium carbonate, potassium carbonate, magnesium carbonate and calcium carbonate, as well as phosphates such as sodium phosphate and potassium phosphate. Particularly preferable among them are sodium chloride, potassium chloride, magnesium chloride, calcium chloride, aluminum chloride, sodium sulfate, potassium sulfate, magnesium sulfate and aluminum sulfate. The blend ratio of the inorganic salt used in the present invention is 0.1–8 wt %, preferably 0.5–5 wt %. The blend ratio ranges less than 0.1 wt % and more than 8 wt % are not preferable because then the emulsion cannot be stabilized.

In the present invention, it is sufficient to use at least one type from among the aforementioned water soluble polymers, amino acid salts or inorganic salts. However, two or more types of water soluble polymers, amino acid salts or inorganic salts may be used, and a mixture of a plurality of water soluble polymers, amino acid salts or inorganic salts can be used as well.

In the present invention, it is preferable to blend in hydrophobic powder in addition to the aforementioned essential ingredients. Hydrophobic powder is obtained by treating silicone resin powder or organic powder and inorganic powder to make them hydrophobic. The most preferable powder is hydrophobic powder obtained by treating silicone resin powder and titanium dioxide powder to give them hydrophobicity.

Examples of the powder used in the hydrophobicity treatment are: inorganic powders including talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate, magnesium, silica, zeolite, barium sulfate, burned calcium sulfate (calcined gypsum), calcium phosphate, fluorine-apatite, hydroxyapatite, ceramic powder, metal soap (zinc myristate, calcium palmitate, aluminum stearate) and boron nitride; organic powders including polyamide resin powder (nylon powder), polyethylene powder, polymethyl methacrylate powder, polystyrene powder, styrene/acrylic acid copolymer resin powder, benzoguanamine resin powder, polyethylene tetrafluoride powder and cellulose powder; inorganic white pigments including silicone resin powder, titanium dioxide and zinc oxide; inorganic red pigments including iron oxide (red iron oxide) and iron titanate; inorganic brown pigments including γ-iron oxide; inorganic yellow pigments including yellow iron oxide and loess; inorganic black pigments including black iron oxide, carbon black and low oxides of titanium; inorganic purple pigments including mango violet and cobalt violet; inorganic green pigments including chrome oxide, chrome hydroxide and cobalt titanate; inorganic blue pigments including ultramarine blue and Berlin blue; pearl pigments including titanium oxide-coated mica, titanium oxide-coated bismuth oxychloride, titanium oxide-coated talc, colored titanium oxide-coated mica, bismuth oxychloride and fish scale flakes; metal powder pigments including aluminum powder and copper powder; organic pigments including red 201, red 202, red 204, red 205, red 220, red 226, red 228, red 405, orange 203, orange 204, yellow 205, yellow 401 and blue 404; zirconium, barium or aluminum lake organic pigments including red 3, red 104, red 106, red 227, red 230, red 401, red 505, orange 205, yellow 4, yellow 5, yellow 202, yellow 203, green 3 and blue 1; and natural colors such as chlorophyll and β-carotene.

The method for the hydrophobicity treatment is not limited and can be any method which can give water repellency. For example, conventional surface treatment methods such as the vapor phase method, liquid phase method, autoclave method and mechanochemical method can be used.

For example, when adding the hydrophobicity treatment agent to the raw material powder, the agent can be diluted in an appropriate solvent (dichloromethane, chloroform, hexan, ethanol, xylene and volatile silicone, etc.) before the addition or it can be added directly. For mixing and stirring the powder and the treatment agent, a ball mill, hogersite ball mill, vibration ball mill, attritor, pot mill, rod mill, pan mill, homegenizer, homodisper, Henshell mixer, Nauta mixer, etc. can be used. Furthermore, a method in which activity on the powder surface is used to polymerize cyclic organosiloxane on the powder surface at a low temperature of 100° C. or lower using the vapor phase method (Tokko Hei 1-54380) and a method in which a pendant group such as glycerol monoallyl ether is added to the Si—H part of the silicone polymer on the surface after said method (Tokko Hei 1-54381) can be used as well.

The hydrophobic treatment agent is not particularly limited. Examples include low viscosity-high viscosity oil-form polysiloxane treatment powders such as fatty acid dextrin treatment powder, trimethylsiloxy silicic acid treatment powder, perfluoroalkyl modified trimethylsiloxy silicic acid treatment powder, methylphenylsiloxy silicic acid treatment powder, perfluoroalkyl modified methylphenylsiloxy silicic acid treatment powder, dimethyl polysiloxane, diphenyl polysiloxane and methylphenyl polysiloxane; treatment powders consisting of organic silyl compound or its fluorine-substituted derivative such as gum-like polysiloxane treatment powder, methylhydrogen polysiloxane treatment powder, perfluoroalkyl modified methylhydrogen polysiloxane treatment powder, methyltrichlorosilane, methyltrialkoxysilane, hexamethyldisilane, dimethyldichlorosilane, dimethyldialkoxysilane, trimethylchlorosislane and trimethylalkoxysilane; treatment powders consisting of organic modified silane or its fluorine-substituted derivative such as ethyltrichlorosilane, ethyltrialkoxysilane, propyltrichlorosilane, propyltrialkoxysilane, hexyltrichlorosilane, hexytrialkoxysilane, long-chain alkyltrichlorosilane and long-chain alkyltriethoxysilane; amino modified polysiloxane treatment powder, perfluoroalkyl modified polysiloxane treatment powder, fluorinated phosphoric acid and fluorinated phosphoric ester treatment powder.

One or more types of these hydrophobic powders can be used. Any hydrophobicity treatment powder that can be used in cosmetics in general is effective and the selection is not limited to the aforementioned ingredients. The blend ratio of the hydrophobic powder in the present invention is preferably 0.5–15 wt %, more preferably 1–10 wt %.

In addition to the aforementioned essential ingredients, ingredients usually used in cosmetics, such as humectants, ultraviolet light absorbents, perfumes, antioxidants, preservatives/anti-molding agents, extender pigments and coloring pigments, can be used as necessary in the emulsified composition of the present invention if they are used within a range which does not deteriorate the effects of the invention.

The applications of the emulsified composition of the present invention are not limited. It is utilized as an emulsified cosmetic, preferably a skin cosmetic or a hair cosmetic. Generally, the present invention has higher significance in terms of the stability of the emulsified composition when it is used in a hair cosmetic with a high alcohol content (with a alcohol content of 6 wt % or more, preferably 10 wt % or more, more preferably 30 wt % or more).

EXAMPLES

Further details of the present invention are described below by referring to examples and comparative examples. The present invention is not limited to these examples. The units of the blend ratios are weight percent.

Examples 1–5, comparative examples 1–5

Cream, an emulsified composition, was prepared according to the recipe shown in Table 1. The obtained cream was evaluated with a stability test and an actual use test by a female specialist panel (ten women). For the stability test, the appearance after allowing to stand for one month at 50° C. was evaluated and for the actual use test the feeling at the time of use was evaluated. The criteria for each test are shown below. The results are shown in Table 1.

[Evaluation criteria for the stability test]

◯: No separation was observed.

Δ: Almost no separation was observed.

X: Separation of the liquid phase (oil phase or water phase) occurred.

[Criteria for the usability]

○: Seven or more women judged that the sample was glossy, moist and not sticky and had excellent usability.

Δ: Three or more and less than seven women judged that the sample was glossy, moist and not sticky and had excellent usability.

X: Three or less women judged that the sample was glossy, moist and not sticky and had excellent usability.

TABLE 1

|  | Example | | | | | Comparative example | | | | |
|---|---|---|---|---|---|---|---|---|---|---|
|  | 1 | 2 | 3 | 4 | 5 | 1 | 2 | 3 | 4 | 5 |
| (1) Dimethyl polysiloxane oil (20 cps) | 30 | 30 | 30 | 20 | 20 | 30 | 30 | 30 | 30 | 30 |
| (2) Polyether modified silicone ([Chemical formula 3]) | 5 | 5 | 5 | 8 | 8 | 5 | 5 | 5 | 5 | 5 |
| (3) Ion exchanged water | 34 | 34 | 30 | 38 | 37 | 35 | 35 | 34.95 | 30 | 30 |
| (4) Ethanol | 30 | 30 | 30 | 30 | 30 | 30 | 30 | 26 | 15 | 5 |
| (5) Sodium glutamate Na | 1 | — | — | 0.5 | 0.5 | — | 0.05 | — | — | — |
| (6) Potassium chloride inorg | — | 1 | — | 0.5 | 0.5 | — | — | 9 | — | — |
| (7) Polyethylene glycol polymer (molecular weight 6,000) | — | — | 5 | 3 | 3 | — | — | — | 25 | — |
| (8) Hydrophobic powder | — | — | — | — | 1 | — | — | — | — | 0.1 |
| Stability | ○ | ○ | ○ | ○ | ○ | X | X | X | ○ | X |
| Usability | ○ | ○ | ○ | ○ | ○ | ○ | ○ | X | X | X |

(Preparation method)

The oil phase was prepared first by mixing and dispersing (2) in (1). The water phase (3) and/or (4) into which (5), (6) or (7) or alternately (5), (6) and (7) or (5), (6), (7) and (8) was dissolved was then gradually added at room temperature while a high speed stirrer was used to obtain the target emulsified composition. For the polyether modified silicone, one represented by the following [Chemical formula 2] was used. For the hydrophobic powder, silicone resin powder was used.

[Chemical formula 2]

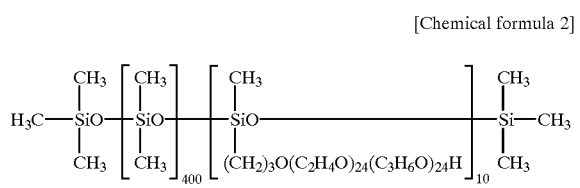

Molecular weight: 55,000; polyoxyalkylene content: 45%

Example 6

Lotion

| (1) Liquid paraffin | 6.0 |
| --- | --- |
| (2) Decamethylcyclopentasiloxane | 10.0 |
| (3) 1,3-butylene glycol | 3.0 |
| (4) Polyether modified silicone ([Chemical formula 3]) | 6.0 |
| (5) Ion exchanged water | 73.0 |
| (6) Sodium glutamate | 2.0 |
| (7) Paraben | Appropriate amount |
| (8) Antioxidant | Appropriate amount |
| (9) Perfume | Appropriate amount |

(Preparation method)

The oil phase was prepared first by mixing and dispersing (1), (2), (4) and (9). The water phase, prepared by dissolving (3), (5), (6), (7) and (8), was then gradually added at room temperature while a high speed stirrer was used to obtain the target lotion. Similar to Examples 1–5, the usability of this lotion was ○; that is, it gave gloss when applied on the skin, had a moist touch and was not sticky. It also had excellent stability (○).

For the polyether modified silicone, one represented by the following [Chemical formula 3] was used.

[Chemical formula 3]

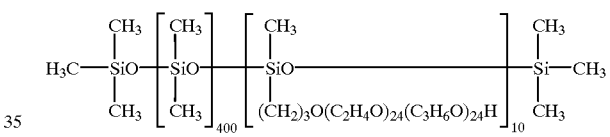

Molecular weight: 55,000; polyoxyalkylene content: 45%

Example 7

Emulsion type hair treatment agent

| (1) Isoparaffin | 30.0 |
| --- | --- |
| (2) Dimethyl polysiloxane (500CS) | 10.0 |
| (3) Glycerol | 5.0 |
| (4) Polyether modified silicone ([Chemical formula 4]) | 8.0 |
| (5) Ion exchanged water | 25.0 |
| (6) Ethanol | 20.0 |
| (7) Sodium chloride | 2.0 |
| (8) Paraben | Appropriate amount |
| (9) Antioxidant | Appropriate amount |
| (10) Perfume | Appropriate amount |

(Preparation method)

The oil phase was prepared first by mixing and dispersing (I), (2), (4) and (10). The water phase, prepared by dissolving (3), (5), (6), (7) , (8) and (9), was then gradually added at room temperature while a high speed stirrer was used to obtain the target emulsion type hair treatment agent. The usability of this emulsion type hair treatment agent was ○; that is, it gave gloss when applied on the hair, had a moist touch and was not sticky. It also had excellent stability (○).

For the polyether modified silicone, one represented by the following [Chemical formula 4] was used.

[Chemical formula 4]

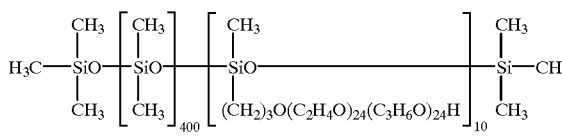

Molecular weight: 55,000; polyoxyalkylene content: 45%

Example 8
Emulsified foundation

| | | |
|---|---|---|
| (1) | Squalane | 2.0 |
| (2) | Dimethyl polysiloxane (6CS) | 20.0 |
| (3) | Propylene glycol | 5.0 |
| (4) | Polyether modified silicone ([Chemical formula 6]) | 4.0 |
| (5) | Ion exchanged water | 26.0 |
| (6) | Ethanol | 8.0 |
| (7) | Polyethylene glycol (molecular weight: 3,000) | 5.0 |
| (8) | Titanium dioxide treated with dextrin palmitate | 10.0 |
| (9) | Mica treated with dextrin palmitate | 10.0 |
| (10) | Talc treated with dextrin palmitate | 5.0 |
| (11) | Iron oxide treated with dextrin palmitate | 5.0 |
| (12) | Ethyl paraben | Appropriate amount |
| (13) | Antioxidant | Appropriate amount |
| (14) | Perfume | Appropriate amount |

(Preparation method)

The oil phase was prepared first by mixing and dispersing (1), (2), (4) and (7)-(14). The water phase, prepared by dissolving (3), (5) and (6), was then gradually added at room temperature while a high speed stirrer was used to obtain the target emulsified foundation. The usability of this emulsified foundation was ○; that is, it gave gloss when applied on the skin, had a moist touch and was not sticky. It also had excellent stability (○).

For the polyether modified silicone, one represented by the following [Chemical formula 5] was used.

[Chemical formula 5]

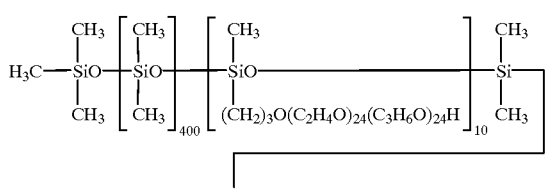

Molecular weight: 58,000; polyoxyalkylene content: 47%

Example 6
Cream

| | | |
|---|---|---|
| (1) | Liquid paraffin | 5.0 |
| (2) | Decamethylcyclopentasiloxane | 25.0 |
| (3) | 1,3-butylene glycol | 5.0 |
| (4) | Polyether modified silicone ([Chemical formula 6]) | 1.0 |
| (5) | Ion exchanged water | 54.0 |
| (6) | Ethanol | 5.0 |
| (7) | Sodium glutamate | 2.0 |
| (8) | Titanium dioxide powder with hydrophobicity treatment | 3.0 |
| (9) | Paraben | Appropriate amount |
| (10) | Antioxidant | Appropriate amount |
| (11) | Perfume | Appropriate amount |

(Preparation method)

The oil phase was prepared first by mixing and dispersing (1), (2), (4) and (11). The water phase, prepared by dissolving (3), (5), (6), (7) , (8), (9) and (10), was then gradually added at room temperature while a high speed stirrer was used to obtain the target cream. The usability of this lotion was ○; that is, it gave gloss when applied on the skin, had a moist touch and was not sticky. It also had excellent stability (○).

For the polyether modified silicone, one represented by the following [Chemical formula 6] was used.

[Chemical formula 6]

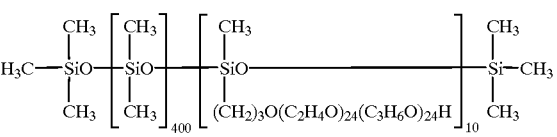

Molecular weight: 55,000; polyoxyalkylene content: 45%

Example 10
Lotion

| | | |
|---|---|---|
| (1) | Liquid paraffin | 6.0 |
| (2) | Decamethylcyclopentasiloxane | 10.0 |
| (3) | 1,3-butylene glycol | 3.0 |
| (4) | Polyether modified silicone ([Chemical formula 7]) | 6.0 |
| (5) | Ion exchanged water | 73.0 |
| (6) | Polyethylene glycol (molecular weight 3,000) | 2.0 |
| (7) | Paraben | Appropriate amount |
| (8) | Antioxidant | Appropriate amount |
| (9) | Perfume | Appropriate amount |

(Preparation method)

The oil phase was prepared first by mixing and dispersing (1), (2), (4) and (9). The water phase, prepared by dissolving (3), (5), (6), (7) and (8), was then gradually added at room temperature while a high speed stirrer was used to obtain the target lotion. Similar to Examples 1–5, the usability of this lotion was ○; that is, it gave gloss when applied on the skin, had a moist touch and was not sticky. It also had excellent stability (○).

For the polyether modified silicone, one represented by the following [Chemical formula 7] was used.

[Chemical formula 7]

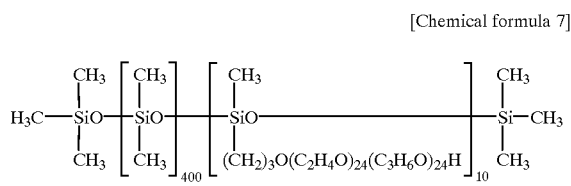

Molecular weight: 55,000; polyoxyalkylene content: 45%

Example 11

Lotion

| (1) Squalane | 6.0 |
| --- | --- |
| (2) Decamethylcyclopentasiloxane | 10.0 |
| (3) 1,3-butylene glycol | 3.0 |
| (4) Polyether modified silicone ([Chemical formula 8]) | 6.0 |
| (5) Ion exchanged water | 73.0 |
| (6) Sodium chloride | 2.0 |
| (7) Paraben | Appropriate amount |
| (8) Antioxidant | Appropriate amount |
| (9) Perfume | Appropriate amount |

(Preparation method)

The oil phase was prepared first by mixing and dispersing (1), (2), (4) and (9). The water phase, prepared by dissolving (3), (5), (6), (7) and (8), was then gradually added at room temperature while a high speed stirrer was used to obtain the target lotion. Similar to Examples 1–5, the usability of this lotion was ○; that is, it gave gloss when applied on the skin, had a moist touch and was not sticky. It also had excellent stability (○).

For the polyether modified silicone, one represented by the following [Chemical formula 8] was used.

[Chemical formula 8]

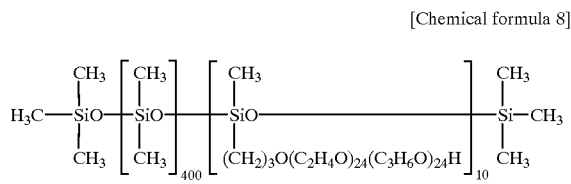

Molecular weight: 55,000; polyoxyalkylene content: 45%

INDUSTRIAL APPLICABILITY OF THE INVENTION

According to the present invention, it is possible to provide an emulsified composition which gives gloss to the hair or skin, is moist but not sticky and exhibits excellent stability by using, as the emulsifier, polyether modified silicone rather than a surfactant or an organic modified clay mineral.

What is claimed is:

1. A water-in-oil emulsified composition comprising:

(I) one or more polyether modified silicones represented by the following Chemical formula:

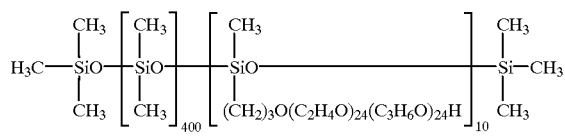

(II) oil, (III) water or water and ethyl alcohol and, (IV) either (a) a water soluble polymer with a molecular weight of 2,000–300,000 whose content is 0.1–20 wt % of the total emulsified composition and (b) an organic salt whose content is 0.1–8 wt % of the total emulsified composition, and (c) an amino acid salt whose content is 0.1–8 wt % of the total emulsified composition, or (a) alone, or (c) alone, or (a) and (b), or (b) and (c).

2. The water-in-oil emulsified composition of claim 1 wherein said water soluble polymer is polyethylene glycol, said amino acid salt is sodium glutamate and said inorganic salt is sodium chloride, potassium chloride, magnesium chloride, calcium chloride, aluminum chloride, sodium sulfate, potassium sulfate, magnesium sulfate or aluminum sulfate.

3. The water-in-oil emulsified composition of claim 1 which additionally contains hydrophobic powder.

4. The water-in-oil emulsified composition of claim 1, wherein said emulsified composition is a skin cosmetic.

5. The water-in-oil emulsified composition of claim 1, wherein said emulsified composition is a hair cosmetic.

6. The water-in-oil emulsified composition of claim 2 which additionally contains hydrophobic powder.

7. The water-in-oil emulsified composition of claim 2 wherein said emulsified composition is a skin cosmetic.

8. The water-in-oil emulsified composition of claim 3 wherein said emulsified composition is a skin cosmetic.

9. The water-in-oil emulsified composition of claim 2 wherein said emulsified composition is a hair cosmetic.

10. The water-in-oil type emulsified composition of claim 3 wherein said emulsified composition is a hair cosmetic.

* * * * *